US010393753B2

(12) United States Patent
Milton et al.

(10) Patent No.: US 10,393,753 B2
(45) Date of Patent: Aug. 27, 2019

(54) HUMAN EXHALED AEROSOL DROPLET BIOMARKER SYSTEM AND METHOD (71) Applicants: Donald K. Milton, University Park, MD (US); Ian M. White, Ellicott City, MD (US)

(72) Inventors: Donald K. Milton, University Park, MD (US); Ian M. White, Ellicott City, MD (US)

(73) Assignee: University of Maryland, College Park, College Park, MD (US)

( * ) Notice: Subject to any disclaimer, the term of this patent is extended or adjusted under 35 U.S.C. 154(b) by 102 days.

(21) Appl. No.: 15/455,873

(22) Filed: Mar. 10, 2017

(65) Prior Publication Data

US 2017/0184609 A1    Jun. 29, 2017

Related U.S. Application Data (62) Division of application No. 14/017,764, filed on Sep. 4, 2013, now Pat. No. 9,617,582.

(60) Provisional application No. 61/726,423, filed on Nov. 14, 2012, provisional application No. 61/696,641, filed on Sep. 4, 2012.

(51) Int. Cl.
| C12P 19/34 | (2006.01) |
| G01N 33/68 | (2006.01) |
| C12Q 1/6804 | (2018.01) |
| G01N 33/543 | (2006.01) |
| C12Q 1/6853 | (2018.01) |
| G01N 33/53 | (2006.01) |

(52) U.S. Cl.
CPC ....... *G01N 33/6863* (2013.01); *C12Q 1/6804* (2013.01); *C12Q 1/6853* (2013.01); *G01N 33/5308* (2013.01); *G01N 33/54366* (2013.01); *G01N 2333/52* (2013.01); *G01N 2333/525* (2013.01); *G01N 2333/545* (2013.01); *G01N 2333/5418* (2013.01); *G01N 2333/5421* (2013.01); *G01N 2333/5437* (2013.01); *G01N 2333/57* (2013.01); *G01N 2800/122* (2013.01); *G01N 2800/26* (2013.01)

(58) Field of Classification Search
CPC ............... C12Q 1/6804; C12Q 1/6853; G01N 2333/52; G01N 2333/525; G01N 2333/5418; G01N 2333/5421; G01N 2333/5437; G01N 2333/545; G01N 2333/57; G01N 2800/122; G01N 2800/26; G01N 33/5308; G01N 33/54366; G01N 33/6863
USPC .................................................... 435/91.2
See application file for complete search history.

(56) References Cited

U.S. PATENT DOCUMENTS

| 4,250,890 | A | 2/1981 | Jones et al. |
| 6,363,772 | B1 | 4/2002 | Berry |
| 6,609,068 | B2 | 8/2003 | Cranley et al. |
| 6,712,881 | B2 | 3/2004 | Hering et al. |
| 7,118,537 | B2 | 10/2006 | Baddour |
| 7,153,272 | B2 | 12/2006 | Talton |
| 7,241,989 | B2 | 6/2007 | Miller et al. |
| 7,297,120 | B2 | 11/2007 | Tsukashima et al. |
| 7,347,825 | B2 | 3/2008 | Vaughan et al. |
| 7,364,553 | B2 | 4/2008 | Paz et al. |
| 7,380,550 | B2 | 6/2008 | Sexton et al. |
| 7,547,285 | B2 | 6/2009 | Kline |
| 7,819,803 | B2 | 10/2010 | Burch et al. |
| 7,972,277 | B2 | 7/2011 | Oki et al. |
| 7,992,422 | B2 | 8/2011 | Leddy et al. |
| 8,250,903 | B2 | 8/2012 | McDevitt et al. |
| 8,316,852 | B2 | 11/2012 | Pouteau et al. |
| 8,368,883 | B2 | 2/2013 | Palmskog et al. |
| 8,491,494 | B2 | 7/2013 | Kline et al. |
| 8,627,821 | B2 | 1/2014 | Edwards et al. |
| 8,705,029 | B2 | 4/2014 | Palmskog et al. |
| 8,801,838 | B2 | 8/2014 | Hering et al. |
| 2007/0053842 | A1 | 8/2007 | Okpala |
| 2009/0269767 | A1 | 10/2009 | Soderlund et al. |
| 2010/0087749 | A1 | 4/2010 | Tovey |
| 2010/0242633 | A1 | 9/2010 | McDevitt et al. |
| 2010/0297635 | A1* | 11/2010 | Olin ...................... A61B 5/411 435/6.11 |
| 2010/0324439 | A1 | 12/2010 | Davenport |
| 2012/0212735 | A1 | 8/2012 | Palmskog et al. |
| 2014/0288454 | A1 | 9/2014 | Paz et al. |

FOREIGN PATENT DOCUMENTS

| DE | 102007012210 | 3/2007 |
| EP | 2108456 | 10/2009 |
| EP | 2361387 | 3/2011 |
| WO | WO 2007120644 | 10/2007 |

(Continued)

OTHER PUBLICATIONS

Adler M et al. (2003) "A real-time immuno-PCR assay for routine ultrasensitive quantification of proteins," Biochem. Biophys. Res. Commun. 308:240-50.

(Continued)

*Primary Examiner* — Cynthia B Wilder (74) *Attorney, Agent, or Firm* — William C. Schrot; AuerbachSchrot LLC (57) ABSTRACT A system and method for detecting a biomarker in exhaled breath condensate nanodroplets comprises noninvasively collecting exhaled breath condensate nanodroplets of a subject, and analyzing said nanodroplets utilizing immunoquantitative polymerase chain reaction to detect one or more target biomarkers.

12 Claims, 2 Drawing Sheets (56) References Cited

FOREIGN PATENT DOCUMENTS

| WO | WO 2008/106961 | 9/2008 |
|---|---|---|
| WO | WO 2011/029888 | 3/2011 |
| WO | WO 2013/061091 | 5/2013 |

OTHER PUBLICATIONS

Adler M et al. (2008) "Sensitivity by combination: immuno-PCR and related technologies," Analyst 133:702-718.
Alberg AJ and Samet JM (2003) "Epidemiology of lung cancer," Chest. 123:21S-49S.
Almstrand A et al. (2010) "Effect of airway opening on production of exhaled particles," J. Appl. Physiol. 108:584-8.
Almstrand AC et al. (2009) "Airway monitoring by collection and mass spectrometric analysis of exhaled particles," Anal. Chem. 81:662-668.
Almstrand AC et al. (2012) "TOF-SIMS analysis of exhaled particles from patients with asthma and healthy controls," Eur. Respir. J. pp. 59-66.
Aziz N et al. (1999) "Variables that affect assays for plasma cytokines and soluble activation markers," Clin. Diagn. Lab Immunol. 6: 89-95.
Barletta J et al. (2009) "Immunomagnetic quantitative immuno-PCR for detection of less than one HIV-1 virion," J. Virol. Methods 157:122-32.
Barletta JM et al. (2005) "Detection of ultra-low levels of pathologic prion protein in scrapie infected hamster brain homogenates using real-time immuno-PCR," J. Virol. Methods 127:154-64.
Bayley DL et al. (2008) "Validation of assays for inflammatory mediators in exhaled breath condensate," Eur. Respir. J. 31:943-948.
Broding HC et al. (2009) "Comparison between exhaled breath condensate analysis as a marker for cobalt and tungsten exposure and biomonitoring in workers of a hard metal alloy processing plant," Int. Arch. Occup. Environ. Health. 82:565-573.
Burbulis I et al. (2005) "Using protein-DNA chimeras to detect and count small numbers of molecules," Nat. Methods 2:31-7.
Burbulis I et al. (2007) "Quantifying small numbers of antibodies with a near-universal protein-DNA chimera," Nat. Methods 4:1011-3.
Carpagnano GE et al. (2002) "Interleukin-6 is increased in breath condensate of patients with non-small cell lung cancer," Int. J. Biol. Markers, 17:141-145.
DeMore JP et al. (2009) "Similar colds in subjects with allergic asthma and nonatopic subjects after inoculation with rhinovirus-16," J. Allergy Clin. Immunol. 124:245-252.
Doherty DE (2008) "A review of the role of FEV1 in the COPD paradigm," COPD 5: 310-318.
Drummond GB and Milic-Emili J (2007) "Forty years of closing volume," Br. J. Anaesth. 99:772-4.
Edwards DA et al. (2004) "Inhaling to mitigate exhaled bioaerosols," Proc. Natl. Acad. Sci. USA 101:17383-17388.
Effros RM et al. (2002) "Dilution of respiratory solutes in exhaled condensates," Am. J. Respir. Crit. Care Med. 165:663-669.
Effros RM et al. (2005) "Epithelial lining fluid solute concentrations in chronic obstructive lung disease patients and normal subjects," J. Appl. Physiol. 99:1286-1292.
Fabian P et al. (2008) "Influenza virus in human exhaled breath: an observational study," PLoS ONE 3:e2691(16 pages).
Fabian P et al. (2009) "Airborne influenza virus detection with four aerosol samplers using molecular and infectivity assays: considerations for a new infectious virus aerosol sampler," Indoor Air 19:433-441.
Fabian P et al. (2009) "An optimized method to detect influenza virus and human rhinovirus from exhaled breath and the airborne environment," J. Envir. Monitoring 11:314-7.
Fabian P et al. (2011) "Origin of exhaled breath particles from healthy and human rhinovirus-infected subjects," J. Aerosol. Med. Pulm. Drug Deliv. 24:137-147.
Fairchild CI and Stampfer JF (1987) "Particle concentration in exhaled breath," Am. Ind. Hyg. Assoc. J. 48:948-949.
Fennelly KP et al. (2004) "Cough-generated aerosols of Mycobacterium tuberculosis: a new method to study infectiousness," Am. J. Respir. Crit. Care Med. 169:604-609.
Garey KW et al. (2004) "Markers of inflammation in exhaled breath condensate of young healthy smokers," Chest. 125: 22-26.
Goldoni M et al. (2008) "Chromium in exhaled breath condensate and pulmonary tissue of non-small cell lung cancer patients," Int. Arch. Occup. Environ. Health, 81:487-493.
Han T et al. (2010) "Performance of an Electrostatic Precipitator with Superhydrophobic Surface when Collecting Airborne Bacteria," Aerosol Sci. Technol. 44:339-348.
Holmgren H et al. (2010) "Size distribution of exhaled particles in the range from 0.01 to 2.0 mu m," J. Aerosol Sci. 41:439-46.
Horvath I et al. (2005) "Exhaled breath condensate: methodological recommendations and unresolved questions," Eur. Respir. J. 26:523-48.
Horvath I et al. (2009) "Exhaled biomarkers in lung cancer," Eur. Respir. J. 34:261-275.
Houseman EA et al. (2006) "A nonstationary negative binomial time series with time-dependent covariates: Enterococcus counts in Boston Harbor," J. Am. Stat. Assoc. 101:1365-1376.
Huynh KN et al. (2008) "A new method for sampling and detection of exhaled respiratory virus aerosols," Clin. Infect. Dis. 46:93-95.
Johnson GR and Morawska L (2009) "The mechanism of breath aerosol formation," J. Aerosol Med. Pulm. Drug Deliv. 22:229-237.
Kazani S and Israel E (2010) "Exhaled breath condensates in asthma: diagnostic and therapeutic implications," J. Breath Res. 4:047001.
Kietzmann D et al. (1993) "Hydrogen peroxide in expired breath condensate of patients with acute respiratory failure and with ARDS," Intensive Care Med. 19:78-81.
King M et al. (1985) "Clearance of mucus by simulated cough," J. Appl. Physiol. 58:1776-1782.
Larsson P et al. (2012) "Surfactant protein A and albumin in particles in exhaled air," Respir. Med. 106:197-204.
Leung TF et al. (2004) "Increased macrophage-derived chemokine in exhaled breath condensate and plasma from children with asthma," Clin Exp Allergy, 34:786-791.
Liu J and Thomas PS (2007) "Relationship between exhaled breath condensate volume and measurements of lung volumes," Respiration 74:142-145.
Liu Y and Daum PH (2000) "The effect of refractive index on size distributions and light scattering coefficients derived from optical particle counters," J. Aerosol. Sci. 31:945-957.
Loukides S et al. (2011) "Exhaled breath condensate in asthma: from bench to bedside," Curr. Med. Chem. 18:1432-1443.
MacDowell AL and Bacharier LB (2005) "Infectious triggers of asthma," Immunol. Allergy Clin. North Am. 25:45-66.
Mainelis G et al. (2002) "Design and Collection Efficiency of a New Electrostatic Precipitator for Bioaerosol Collection," Aerosol Sci. Technol. 36:1073-1085.
Mannino DM and Braman S (2007) "The epidemiology and economics of chronic obstructive pulmonary disease," Proc. Am. Thorac. Soc. 4: 502-506.
Markey AL et al. (2010) "High-throughput droplet PCR," Methods 50:277-81.
Martinez et al. (2004) "Exposure assessment and analysis for biological agents," Grana, 43(4):193-208.
McKenzie et al. (2012) "Collection of Aerosolized Human Cytokines Using Teflon Filters," Plos One 7:e35814 (11 pages).
McKenzie JH (2010) "Methods for environmental endotoxin assay and respiratory biomarker measurement," Lowell, MA: University of Massachusetts Lowell, School of Health & Environment.
McKenzie JH et al. (2009) "Use of Teflon filters improves collection efficiency of aerosolized cytokines," Am. J. Respir. Crit. Care Med. 179:A1365.
Montuschi (2007) "Analysis of exhaled breath condensate in respiratory medicine; methodological aspects and potential clinical applications," Therapeutic Advances in Respiratory Disease, 1(1):5-23.

(56) References Cited

OTHER PUBLICATIONS

Morawska L et al. (2009) "*Size distribution and sites of origin of droplets expelled from the human respiratory tract during expiratory activities,*" J. Aerosol. Sci. 40:256-269.

Moriarty JA and Grotberg JB (1999) "*Flow-induced instabilities of a mucus-serous bilayer,*" J. Fluid Mech. 397:1-22.

Mutti A et al. (2006) "*Exhaled metallic elements and serum pneumoproteins in asymptomatic smokers and patients with COPD or asthma,*" Chest. 129:1288-1297.

Nicas M et al. (2005) "*Toward understanding the risk of secondary airborne infection: emission of respirable pathogens,*" J. Occup. Environ. Hyg. 2: 143-154.

Niemeyer CM et al. (2005) "*Immuno-PCR: high sensitivity detection of proteins by nucleic acid amplification,*" Trends Biotechno. 23:208-216.

Niemeyer CM et al. (2007) "*Detecting antigens by quantitative immuno-PCR,*" Nat. Protoc. 2:1918-930.

Ottesen EA et al. (2006) "*Microfluidic digital PCR enables multigene analysis of individual environmental bacteria,*" Science 314:1464-7.

Panicker G et al. (2007) "*Effect of storage temperatures on the stability of cytokines in cervical mucous,*" Cytokine 37:176-179.

Papineni RS and Rosenthal FS (1997) "*The size distribution of droplets in the exhaled breath of healthy human subjects,*" J. Aerosol Med. 10:105-16.

Pinnick RG et al. (2000) "*Response Characteristics of the Particle Measuring Systems Active Scattering Aerosol Spectrometer Probes,*" London: Taylor & Francis, pp. 334-352.

Pitkaranta A and Hayden FG (1998) "*Rhinoviruses: important respiratory pathogens,*" Ann. Med. 30:529-537.

Rajkovic A. (2006) "*Immunoquantitative real-time PCR for detection and quantification of Staphylococcus aureus Enterotoxin B in foods,*" Appl. Environ. Microbiol., 72:6593-6599.

Rennard SI (1998) "*COPD: overview of definitions, epidemiology, and factors influencing its development,*" Chest. 113:235S-241S.

Rosias P et al. (2004) "*Childhood asthma: exhaled markers of airway inflammation, asthma control score, and lung function tests,*" Pediatr. Pulmonol. 38:107-114.

Rosias P et al. (2004) "*Exhaled breath condensate: a space odessey, where no one has gone before,*" Eur. Respir. J. 24:189-190.

Rudnick SN and Milton DK (2003) "*Risk of indoor airborne infection transmission estimated from carbon dioxide concentration,*" Indoor Air. 13:237-245.

Sack U et al. (2006) "*Multiplex analysis of cytokines in exhaled breath condensate,*" Cytometry A. 69:169-72.

Sapey E et al. (2008) "*The validation of assays used to measure biomarkers in exhaled breath condensate,*" Eur. Respir. J. 32:1408-1409.

Schaerli Y et al. (2009) "*Continuous-flow polymerase chain reaction of single-copy DNA in microfluidic microdroplets,*" Anal. Chem. 81:302-6.

Schwarz K et al. (2010) "*Characterization of exhaled particles from the healthy human lung—a systematic analysis in relation to pulmonary function variables,*" J. Aerosol Med. Pulm. Drug Deliv. 23:371-9.

Shahid SK et al. (2002) "*Increased interleukin-4 and decreased interferon-gamma in exhaled breath condensate of children with asthma,*" Am. J. Respir. Crit. Care Med., 165:1290-1293.

Srisa-Art M et al. (2009) "*High-throughput confinement and detection of single DNA molecules in aqueous microdroplets,*" Chem. Commun. (Cam b) 6548-50.

Stanley WM (1944) "*The size of influenza virus,*" J. Exp. Med. 79:267-283.

Thavasu PW et al. (1992) "*Measuring cytokine levels in blood. Importance of anticoagulants, processing, and storage conditions,*" J. Immunol. Methods 153:115-124.

Urban FL (2008) "*Review of the NAEPP 2007 Expert Panel Report (EPR-3) on Asthma Diagnosis and Treatment Guidelines,*" J. Manag, Care Pharm. 14: 41-49.

Verreault D et al. (2008) "*Methods for sampling of airborne viruses,*" Microbiol. Mol. Biol. Rev. 72:413-444.

Wang F and Burns MA (2009) "*Performance of nanoliter-sized droplet-based microfluidic PCR,*" Biomed. Microdevices (10 pages).

Weist S et al. (2010) "*Effects of thawing, refreezing and storage conditions of tissue samples and protein extracts on 2-DE spot intensity,*" Proteomics 10:1515-1521.

Wood SN (2000) "*Modeling and smoothing parameter estimation with multiple quadratic penalties,*" J. Stat. Soc. (B) 62:413-428.

\* cited by examiner

Human exhaled aerosol droplet biomarker system and method

HUMAN EXHALED AEROSOL DROPLET BIOMARKER SYSTEM AND METHOD

CROSS-REFERENCE TO RELATED APPLICATIONS

This application is a divisional of U.S. patent application Ser. No. 14/017,764, filed Sep. 4, 2013, which is based on U.S. Provisional Patent Application Ser. No. 61/696,641, filed Sep. 4, 2012, and Application Ser. No. 61/726,423, filed Nov. 14, 2012, which applications are incorporated herein by reference in their entireties and to which priority is claimed.

FIELD OF THE INVENTION

The present invention relates to a system and method for detection of nonvolatile biomarkers in exhaled breath nanodroplets.

BACKGROUND OF THE INVENTION

Chronic lung diseases are a significant health and economic burden worldwide. For example, chronic obstructive lung disease (COPD) is the fourth leading cause of death in adults (Rennard S I (1998) "*COPD: overview of definitions, epidemiology, and factors influencing its development*," Chest. 113:235S-241S), and lung cancer has the highest mortality of all cancers in both men and women (Alberg A J and Samet J M (2003) "*Epidemiology of lung cancer*," Chest. 123:21S-49S). The common risk factor for both is cigarette smoking. However, only 10-15% of smokers develop COPD and/or lung cancer. Non-invasive efforts to identify biomarkers for such conditions have not been efficient or clinically effective.

Conventional methodologies typically provide for measuring biomarkers in lungs via invasive procedures such as bronchoscopy to obtain samples, carrying the associated costs, discomfort, and risks. Such biomarkers are needed for identifying the environmental factors in the generation and natural history of chronic lung diseases, and would allow for reliably following molecular events that are currently beyond detection using conventional methodologies.

Exhaled biomarkers could serve as a molecular and genetic signature, opening the doors for personalized medicine. Exhaled breath is an aerosol consisting mostly of water vapor, with smaller amounts of volatile, semi-volatile, and non-volatile molecules derived from the upper and lower portions of the respiratory system (Effros R M et al. (2005) "*Epithelial lining fluid solute concentrations in chronic obstructive lung disease patients and normal subjects*," J. Appl. Physiol. 99:1286-1292; Horvath I et al. (2005) "*Exhaled breath condensate: methodological recommendations and unresolved questions*," Eur. Respir. J. 26:523-548).

Cytokines are small, water-soluble signaling proteins produced by cells of the immune system to modulate responses of the immune system such as inflammation. Since inflammation is an underlying condition of many chronic diseases, exhaled cytokines may be considered biomarkers of pulmonary inflammation that could indicate the presence of lung diseases or provide information regarding the current status of the lungs. As such, non-invasive monitoring of lung inflammation through detection and measurement of cytokines in exhaled breath samples would be a promising new approach aimed at addressing the need for an improved understanding, treatment and management of chronic respiratory diseases such as lung cancer, asthma and COPD.

Thus, there has been great interest in the study of exhaled breath condensate (EBC), and in techniques for the collection and analysis of non-volatile compounds (e.g. cytokines) present in the respiratory lining fluid (RLF). Studies of exhaled breath suggest that humans generate fine particles during tidal breathing, but little is known of their origin in the respiratory system. Older studies of exhaled breath primarily detected particles larger than 1 μm due to less sensitive techniques, such as counting particles in photographs of coughs and sneezes (Jennison M W "*Atomizing of Mouth And Nose Secretions into the Air as Revealed by High-Speed Photography, in Aerobiology Publication*," Washington, D.C.: American Association for the Advancement of Science, p. 106), culturing of indicator bacteria exhaled and impacted on plates (Duguid J (1945) "*The numbers and the sites of origin of the droplets expelled during expiratory activities*," Edinburgh Med. J. 52:385-401), and counting slides or filters of exhaled dye droplets under a microscope (Id.; Loudon R G and Roberts R M (1967) "Droplet expulsion from the respiratory tract," Am Rev Respir. Dis. 95:435-442). In such older studies, particles were typically detected only during coughs and sneezes, and not in breath exhaled during tidal breathing.

In more recent studies, it has been shown that approximately 98% of particles produced during tidal breathing are under 1 μm (Fairchild C I and Stampfer J F (1987) "*Particle concentration in exhaled breath*," Am. Ind. Hyg. Assoc. J. 48:948-949; Papineni R S and Rosenthal F S (1997) "*The size distribution of droplets in the exhaled breath of healthy human subjects*," J. Aerosol Med. 10:105-116; Edwards D A et al. (2004) "*Inhaling to mitigate exhaled bioaerosols*," Proc. Natl. Acad. Sci. USA 101:17383-17388; Morawska L et al. (2008) "*Size distribution and sites of origin of droplets expelled from the human respiratory tract during expiratory activities*," J. Aerosol. Sci. 40:256-269). For example, in a previous study of subjects infected with influenza, it was found that the subjects produced 67 to 8500 particles per liter of air, and that 87% of the particles were under 1 μm (Fabian P et al. (2008) "*Influenza virus in human exhaled breath: an observational study*," PLoS ONE 3:e2691).

Such droplets can be generated by shear forces produced by air flow acting on the airway lining fluid and entraining particles composed of mucus, surfactant, and pathogens (King M et al. (1985) "*Clearance of mucus by simulated cough*," J. Appl. Physiol. 58:1776-1782; Moriarty J A and Grotberg J B (1999) "*Flow-induced instabilities of a mucus-serous bilayer*," J. Fluid Mech. 397:1-22), especially during cough (Leith D et al. (1986) "*Cough*" in M J Macklem (ed). Handbook of Physiology, The Respiratory System, Section 3, Vol. III, Part 1, Bethesda, Md.: American Physiological Society, pp. 315-336). It has been hypothesized that droplets are produced from the destabilization of the lining fluid during the reopening of collapsed small airways and alveoli during breathing (Edwards D A et al. (2004), supra., Proc. Natl. Acad. Sci. USA 101:17383-17388). Another study found that exhaled particle concentrations increased 4- to 18-fold when inhaling deeply and rapidly after a deep exhalation, hypothesizing that the opening of airways and alveoli blocked by fluid during inhalation is a significant source of particles (Johnson G R and Morawska L (2009) "*The mechanism of breath aerosol formation*," J. Aerosol Med. Pulm. Drug Deliv. 22:229-237). Identifying the origin of these particles is important when interpreting studies of exhaled breath biomarkers, including cytokines (Shahid S K et al. (2002) "*Increased interleukin-4 and decreased interferon-gamma in exhaled breath condensate of children with asthma*," Am. J. Respir. Crit. Care Med., 165:1290-1293;

Garey K W et al. (2004) "*Markers of inflammation in exhaled breath condensate of young healthy smokers*," Chest. 125: 22-26; Rosias P P et al. (2004) "*Childhood asthma: exhaled markers of airway inflammation, asthma control score, and lung function tests*," Pediatr. Pulmonol. 38:107-114; Carpagnano G E et al. (2002) "*Interleukin-6 is increased in breath condensate of patients with non-small cell lung cancer*," Int. J. Biol. Markers, 17:141-145; Leung T F et al. (2004) "Increased macrophage-derived chemokine in exhaled breath condensate and plasma from children with asthma," Clin Exp Allergy, 34:786-791; and Rosias P et al. (2004) "*Exhaled breath condensate: a space odessey, where no one has gone before*," Eur. Respir. J. 24:189-190), metals (Broding H C et al. (2009) "*Comparison between exhaled breath condensate analysis as a marker for cobalt and tungsten exposure and biomonitoring in workers of a hard metal alloy processing plant*," Int. Arch. Occup. Environ. Health. 82:565-573; Goldoni M et al. (2008) "*Chromium in exhaled breath condensate and pulmonary tissue of non-small cell lung cancer patients*," Int. Arch. Occup. Environ. Health, 81:487-493; Mutti A et al. (2006) "*Exhaled metallic elements and serum pneumoproteins in asymptomatic smokers and patients with COPD or asthma*," Chest. 129:1288-1297), and pathogens such as viruses (Fabian P et al. (2008), supra., PLoS ONE 3:e2691; Huynh K N et al. (2008) "*A new method for sampling and detection of exhaled respiratory virus aerosols*," Clin. Infect. Dis. 46:93-95) and bacteria (Fennelly K P et al. (2004) "*Cough-generated aerosols of Mycobacterium tuberculosis: a new method to study infectiousness*," Am. J. Respir. Crit. Care Med. 169:604-609).

Collection of EBC samples non-invasively may be accomplished through means whereby a subject breathes normally into a chilled collection device that condenses and collects fluid samples. EBC samples consist of a mixture of three main components (Horvath I et al. (2005), supra., Eur. Respir. J. 26:523-548). The most abundant component (99%) of EBC samples is liquid water formed from the condensation of water vapor present in the warm exhaled air, saturated with water vapor as it leaves the respiratory tract. The second and third components of EBC samples are water-soluble volatile and non-volatile particles that are aerosolized from the respiratory lining fluid and are present in significantly smaller amounts than the water component of EBC samples (Horvath I et al. (2005), supra., Eur. Respir. J. 26:523-548; Kietzmann D et al. (1993) "*Hydrogen peroxide in expired breath condensate of patients with acute respiratory failure and with ARDS*," Intensive Care Med. 19:78-81; Effros R M et al. (2002) "*Dilution of respiratory solutes in exhaled condensates*," Am. J. Respir. Crit. Care Med. 165:663-669; Horvath I et al. (2009) "*Exhaled biomarkers in lung cancer*," Eur. Respir. J. 34:261-275; Kazani S and Israel E (2010) "*Exhaled breath condensates in asthma: diagnostic and therapeutic implications*," J. Breath Res. 4:047001; Loukides S et al. (2011) "*Exhaled breath condensate in asthma: from bench to bedside*," Curr. Med. Chem. 18:1432-1443).

Unfortunately, the significant amount of liquid water present in EBC samples dilutes the inherently low concentrations of non-volatile biomarkers to levels that are at or below the detection threshold of methodologies utilizing conventional assays. Moreover, the inefficient collection of exhaled, nonvolatile submicron particles using conventional EBC collection methods, combined with assay sensitivity limitations currently being used, creates significant problems with reproducibility and validity of biomarker measurements (Horvath I et al. (2005), supra., Eur. Respir. J. 26:523-548; Kazani S and Israel E (2010) "*Exhaled breath condensates in asthma: diagnostic and therapeutic implications*," J. Breath Res. 4:047001; Loukides S et al. (2011), supra., Curr. Med. Chem. 18:1432-1443; Sack U et al. (2006) "*Multiplex analysis of cytokines in exhaled breath condensate*," Cytometry A. 69:169-172; Bayley D L et al. (2008) "*Validation of assays for inflammatory mediators in exhaled breath condensate*," Eur. Respir. J. 31:943-948; Sapey E et al. (2008) "*The validation of assays used to measure biomarkers in exhaled breath condensate*," Eur. Respir. J. 32:1408-1409). For example, the aerosol particle collection efficiency of conventional EBC devices is typically less than 25%.

As a result, conventional systems and methods for biomarker collection and analysis fail to provide sufficient sensitivity and efficiency for detecting cytokines and other non-volatile biomarkers in EBC. The availability of an effective, non-invasive system and methodology able to detect trace amounts of target biomarker(s) would open a new world of possibilities to the diagnosis and management of lung diseases and disorders.

SUMMARY OF THE INVENTION

The present invention is directed to an integrated system and method for detection of nonvolatile biomarkers in exhaled breath nanodroplets of respiratory lining fluid from the distal lung. The disclosed system far exceeds the sensitivity and reliability of conventional exhaled breath condensate collection and assay systems, and includes various innovative components and techniques. The disclosed systems and methodologies are suitable for the diagnosis and management of various diseases and disorders, such as lung cancer, asthma, COPD, tuberculosis, influenza, and HIV/AIDS related respiratory infections.

According to one aspect, specialized breathing maneuvers are utilized (exhalation to residual volume while supine), which increase output of respiratory droplets of distal airway lining fluid containing nonvolatile biomarkers, rather than normal tidal breathing used in conventional methods.

According to another aspect, collection using air pollution techniques is utilized for collection of particle matter (PM) with a range of sizes from nanodroplets through PM 10, rather than condensation of water vapor from exhaled breath as in conventional methods.

According to another aspect, efficient recovery of labile proteins from the collection device is provided, by direct impaction in a liquid and extraction filters. In one implementation, the disclosed system provides for high efficiency nanodroplet collection by impaction into a liquid media. A collection device is provided which maximizes impaction via precise air flow control, combined with collection of the droplets on filters.

According to another aspect, immuno-quantitative polymerase chain reaction (IqPCR) assay is utilized to detect as few as 100 molecules of biomarker.

According to another aspect, optical particle counts are utilized to determine the volume of respiratory fluid droplets generated by each subject, allowing direct standardization of the biomarker results in terms of concentration in lung lining fluid.

The present invention provides for a method for detecting a biomarker in exhaled breath condensate nanodroplets, comprising the steps of: noninvasively collecting exhaled breath condensate (PBC) nanodroplets from a subject; and analyzing said nanodroplets utilizing immuno-quantitative polymerase chain reaction (IqPCR) to detect one or more target biomarkers.

In one implementation, the biomarkers are associated with a respiratory disease, disorder or infection, such as lung cancer, asthma, chronic obstructive pulmonary disease, tuberculosis, influenza, a human immunodeficiency virus (HIV) related infection, and an acquired immune deficiency syndrome (AIDS) related infection. The biomarkers may be cytokines (e.g., such as IFN-gamma, IL-1 beta, IL-7, IL-8, IL-13, and TNF-alpha).

In one implementation, the nanodroplets are impacted into a liquid medium by a collection device during the collection process. The volume of nanodroplets generated by the subject is determined, and a concentration of the detected biomarkers within the collected nanodroplets may then be standardized. In some implementations, the subject is disposed in a supine position during the collection process in order to increase nanodroplet production.

The present invention also provides for a system for detecting nonvolatile biomarkers in exhaled breath nanodroplets. The system comprises a collection device configured to noninvasively collect exhaled breath condensate nanodroplets from a subject, and immuno-quantitative polymerase chain reaction (IqPCR) assay for detecting one or more target biomarkers in the nanodroplets.

In one implementation, the IqPCR assay comprises a microbead having an antibody immobilized thereon, which binds to a particular target biomarker. The IqPCR exhibits at least a 10-fold increase, more preferably at least a 1000-fold increase, in sensitivity in detection of said target biomarkers as compared to enzyme-linked immuno-sorbent assay (ELISA).

The present invention also provides for a microfluidic device for detecting one or more biomarkers in nanodroplets. The microfluidic device comprises a substrate comprising a microchannel having an inlet and an outlet, and a microbead-antibody complex disposed within said microchannel, said microbead-antibody complex configured to detect said biomarker.

In one implementation, the microfluidic device comprises a thermocycler disposed on the substrate and in fluid communication with the microchannel. The thermocycler comprises an IqPCR assay utilizing a DNA-labeled recognition antibody adapted to target biomarkers bound to the microbead-antibody complex. In some embodiments, the microfluidic device is a multiplexed IqPCR device configured to simultaneously detect multiple biomarkers.

DETAILED DESCRIPTION OF THE INVENTION

The present invention is directed to a non-invasive diagnostic system and method to quantitatively measure nonvolatile biomarkers (e.g. proteins such as cytokines, DNA, lipids, etc.) dissolved in respiratory fluid of the lower respiratory tract. The present invention is also directed to a microfluidic multiplexed IqPCR device.

The detection of low concentrations of biomarkers with accuracy and sensitivity in test samples poses a significant problem and is not feasible with conventional immunoassays such as enzyme-linked immuno-sorbent assay (ELISA). By combining immunoassay with nucleic acid amplification, the disclosed methodologies overcome the sensitivity limitations of such conventional techniques. The amplification provided by IqPCR enables the detection of single nucleic acid molecules. In one implementation, a DNA probe hybridized to its template provides exceptional sensitivity and target specificity. IqPCR allows for detection of biological molecules at concentrations as low as 1 femtogram/mL, or even in the attogram level, thus providing a 10- to 1000-fold increase in sensitivity over conventional methods such as ELISA.

The detection of nucleic acids can be achieved at levels of a few molecules using IqPCR. In contrast, the analysis of proteins using conventional methods, such as ELISA, hardly surpasses sensitivity levels below $1 \times 10^{-18}$ mol of the antigen. By combining the enormous amplification power of PCR with antibody-based immuno-assays, sensitivity is substantially enhanced (e.g., see Adler M et al. (2008) "*Sensitivity by combination: immuno-PCR and related technologies,*" Analyst, 133:702-718). IqPCR is based on chimeric conjugates of specific antibodies and nucleic acid molecules. The nucleic acid molecules are used as markers to be amplified by PCR for signal generation. In one implementation, methodologies for conjugating antibodies with DNA such as disclosed by Adler M et al. (2008), supra., Analyst, 133:702-718, are utilized, the disclosure of which is incorporated herein by reference.

The disclosed system and method is in part a synthesis of recent advances in understanding the physiology of aerosol generation by the human lung, specialized aerosol sampling and optical particle counting technology, combined with novel IqPCR technology capable of detection of cytokines at attomolar levels. According to the disclosed methodologies, the IqPCR assays measure cytokines in the low femtogram, and more preferably attogram, quantities per sample (1000 to 100 molecules per sample). Exhaled droplet numbers and size distribution are counted with an optical particle counter designed for breath sampling, measuring lung volumes, especially closing volume, and determining optimal methods for generating large numbers of exhaled droplets from the lower respiratory tract. Exhaled respiratory droplets may be collected with conventional breath condensate and aerosol filter methods (e.g., such as disclosed in McKenzie J H et al. (2012) "*Collection of Aerosolized Human Cytokines Using Telfon® Filters,*" PLoS ONE, Vol. 7, Issue 5, e35814), and then assayed for cytokines in the samples using IqPCR. Cytokine measurements are normalized with total droplet volume determined from optical particle count data. Exhaled breath measurements of respiratory fluid cytokine concentrations are then validated in three groups of subjects, including subjects with COPD, lung cancer, and normal or healthy lungs, by examining concordance with cytokine concentrations in bronchoalveolar lavage fluid (BAL) fluid determined by conventional methods.

The disclosed system and method revolutionizes the field of exhaled biomarker measurement by substantially increasing the sensitivity of biomarker assay, while also increasing the release of biomarkers from the lung by obtaining samples while the subject is in a supine position when performing breathing maneuvers. As a result, the efficiency of both collection methods and assay sensitivity is greatly improved.

Understandings about the physiology of aerosol droplet generation by the lung are utilized in order to increase the output of respiratory fluid droplets. The fundamental features of "airway closure" were described by Dollfuss and colleagues (Dolifuss R E et al. (1967) "*Regional Ventilation of Lung Studied with Boluses of* 133*XENON*," Respiration Physiology 2:234). The lung volume at which airway closure begins during a progressive slow exhalation is termed the closing point (CP), and the volume remaining to residual volume is termed the closing volume (CV). The terminal bronchioles are generally considered the site of airway closure. With airway closure, respiratory tract lining fluid (RTLF) in the terminal bronchiole forms films that rupture when the airway reopens, thereby causing particles to form.

Airway closure maneuvers that involve exhalations to low-lung volumes (near residual volume or RV) may be employed, such that a portion of the terminal bronchioles collapse, temporarily closing the airways. The terminal bronchioles are then reopened upon the next inhalation (see Almstrand A et al. (2010) "*Effect of airway opening on production of exhaled particles*," J. Appl. Physiol. 108:584-8; Schwarz K et al. (2010) "*Characterization of exhaled particles from the healthy human lung—a systematic analysis in relation to pulmonary function variables*," J. Aerosol Med. Pulm. Drug Deliv. 23:371-9; Holmgren H et al. (2010) "*Size distribution of exhaled particles in the range from* 0.01 *to* 2.0 *mu m*," J. Aerosol Sci. 41:439-46). Studies have shown that deep exhalation results in a four- to more than ten-fold increase in concentration, and rapid inhalation may produce a further two- to three-fold increase in concentration (see Fabian P et al. (2011) "*Origin of exhaled breath particles from healthy and human rhinovirus-infected subjects*," J. Aerosol Med. Pulm. Drug Delivery, In Press; Johnson G R and Morawska L (2009), supra., J. Aerosol Med. Pulm. Drug Deliv.; Schwarz K et al. (2010), supra., J. Aerosol Med. Pulm. Drug Deliv. 23:371-9; Papineni R S and Rosenthal F S (1997), supra., J. Aerosol Med. 10:105-16).

In contrast, rapid exhalation has little effect on the measured concentration. Droplet formation occurs in the lower airways as a result of dynamic airway closure, which upon reopening destabilizes the mucous lining of the lower airways, thereby producing tiny droplets which contain sub-micron particles from the lower airways (Johnson G R and Morawska L (2009), supra., J. Aerosol Med. Pulm. Drug Deliv.; Almstrand A et al. (2010), supra., J. Appl. Physiol. 108:584-8; Schwarz K et al. (2010), supra., J. Aerosol Med. Pulm. Drug Deliv. 23:371-9; Edwards D A et al. (2004), supra., Proc. Natl. Acad. Sci. USA 101:17383-8).

In the supine position, because of abdominal contents pushing on the diaphragm, the closing volume is closer to and may exceed the functional residual capacity (FRC). Thus, breathing while in a supine position is believed to increase the output of exhaled droplets of respiratory lining fluid. Thus, in light of this phenomenon, production of RTLF droplets may be further enhanced by combining supine posture with exhalation to RV. Such a breathing maneuver and position of the subject is utilized to increased airway closure and generation of nanodroplets from respiratory fluid, and thus exhaled nanodroplets from the deep lung.

In addition, rather than collect droplets by inefficient, conventional condensation methods, methods adapted from air pollution monitoring are utilized to collect all expired droplets with high efficiency, such as TEFLON® filters (see McKenzie J H et al. (2012), supra., PLoS ONE, Vol. 7, Issue 5, e35814, the disclosure of which is incorporate herein by reference).

In one embodiment, a human exhaled nano-droplet collector such as disclosed in U.S. Pat. No. 8,250,903 is utilized in combination with the methodologies of the present invention. In particular, samples collecting using such collector device are then assayed using IqPCR, as discussed in further detail below.

In other embodiments, a human exhaled nano-droplet collector is utilized with enhanced impaction of collected particles into a liquid medium. Such collection method exhibits >85% collection efficiency at 50 nm into liquid medium. A liquid-impinger collection device is provided, which collects aerosolized particles into a liquid medium through inertial impaction. The use of liquid collection medium prevents desiccation and possible degradation of collected particles. Conventional liquid impinge devices suffer from various disadvantages, such as having a relatively low sample flow rate and high sample collection volume, resulting in considerable dilution of collected particles. The collection device of the present invention, used in combination with IqPCR, substantially reduces sample collection volume required.

Figure 1:
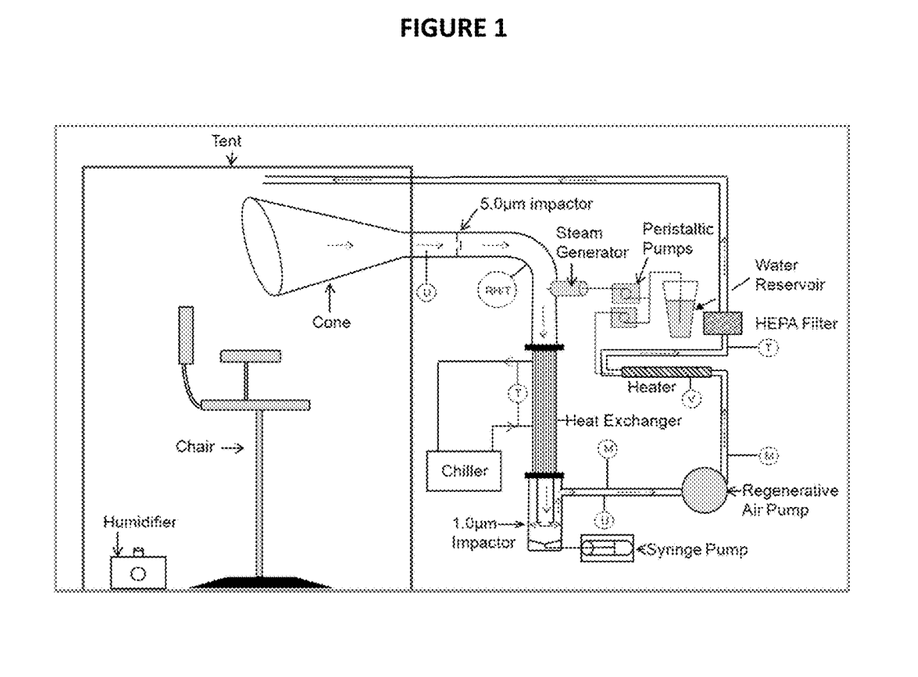
FIG. 1 is a schematic of a device according to the present invention for collecting particles from exhaled breath condensate.

An exemplary collection system according to an embodiment of the present invention is illustrated in FIG. 1. The system includes a cone-shaped inlet for collection of exhaled breath from a subject. The shape and size of the inlet permits the subject to wear a mask or respirator during testing. A seating area is provided for the subject, which may be tented or enclosed. A humidifier is provided within the tented area in order to increase moisture content therein. A 5.0 μm slit inertial impactor collects particles greater than 5 μm. A steam generator, and associated pump and water reservoir, is provided. The steam generator injects a turbulent flow of steam into the flow path in order to increase the relative humidity to near saturation at a relatively warm temperature. This increase in relative humidity makes it possible to subsequently create supersaturation of water vapor by rapidly cooling the high humidity fluid flow using a chiller. In the chiller, water vapor condenses on the small particles in the fluid flow, thereby causing them to grow into larger water droplets which can then be collected downstream with an inertial impactor. Thus, condensation from the steam generator grows remaining particles to a size large enough to be collected by the downstream impactor (e.g., a 1.0 μm slit inertial impactor). The particles are carried along via a regenerative air pump, and ultimately collected in a filter.

In order to substantially lower the minimum detectable and quantifiable cytokine concentration by several thousand orders of magnitude, as compared to conventional methodologies, IqPCR is utilized. Human exhaled breath contains attoliter to femtoliter volume droplets that contain rare protein biomarkers. The total collection over a 20 min sampling period contains but a few picoliters of these droplets. As a result of the small sample volume and relatively low concentration of the potential biomarkers, a subject sample may have at most thousands of protein biomarker molecules, and more typically tens to hundreds of molecules per sample. When diluted by a factor of $10^6$ into a typical volume for an assay (i.e. 50 μL), the resulting attomolar concentrations of most biomarkers are not detectable using conventional immunoassay techniques, such as ELISA or the Luminex assay (wherein typical detection limits range from nanomolar to femtomolar). The utilization of IqPCR for the detection of biomarker proteins in exhaled breath leverages the well-established nucleic acid amplification technique of PCR in order to provide amplification in an immunoassay (see Adler M et al. (2008) "*Sensitivity by combination: immuno-PCR and related technologies,*" Analyst 133:702-718; Niemeyer C M et al. (2005) "*Immuno-PCR: high sensitivity detection of proteins by nucleic acid amplification,*" Trends Biotechno. 23:208-216; Niemeyer C M et al. (2007) "*Detecting antigens by quantitative immuno-PCR,*" Nat. Protoc. 2:1918-930). As noted above, IpPCR is substantially more sensitive than conventional techniques, providing a 10- to 1000-fold increase in sensitivity compared to techniques such as ELISA and mass spectrometry assays. For example, according to a study directed to an IqPCR method for detection of *Staphylococcus aureus* enterotoxin B (SEB), the IqPCR was approximately 1000 times more sensitive (<10 pg ml$^{-1}$) when compared to ELISA using the same couple of capture-detection antibodies (Rajkovic A (2006) "*Immuno quantitative real-time PCR for detection and quantification of Staphylococcus aureus enterotoxin B in foods,*" Appl. Environ. Microbiol., 72(10):6593-6599). In that study, the assay consisted of immunocapture of SEB and real-time PCR amplification of the DNA probe linked to the detection antibody (Id.).

Figure 2:
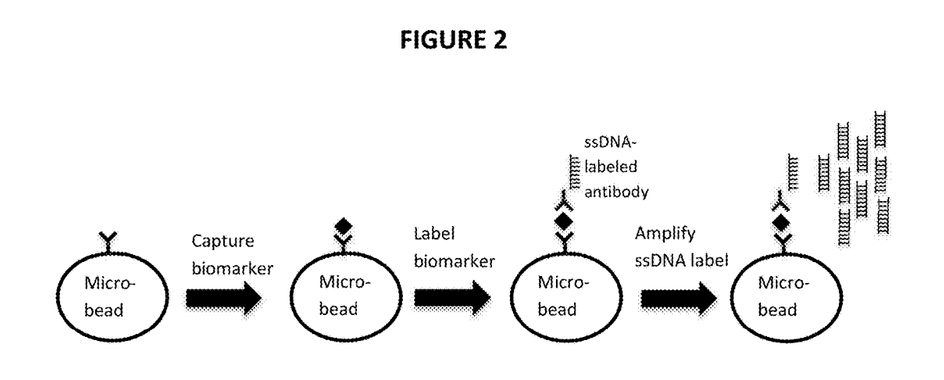
FIG. 2 is a schematic of IqPCR utilizing microbeads for detecting trace amounts of a biomarker.

The immunoassay portion of IqPCR utilized in the present invention resembles in part conventional techniques. Referring to FIG. 2, the sample is applied to a substrate (e.g., microbeads), onto which is immobilized an antibody directed toward the biomarker of interest. After washing, a recognition antibody is applied to target any biomarker proteins captured at the surface. However, whereas ELISA uses an enzyme labeled immunorecognition system, IqPCR uses a custom-synthesized DNA-labeled antibody. As a result, a DNA template marks the captured biomarkers in the assay. The DNA is then amplified using qPCR, which provides several orders of magnitude gain, enabling the detection of very low numbers of biomarker antigens (see Barletta J M et al. (2005) "*Detection of ultra-low levels of pathologic prion protein in scrapie infected hamster brain homogenates using real-time immuno-PCR,*" J. Virol. Methods 127:154-64; Barletta J et al. (2009) "*Immunomagnetic quantitative immuno-PCR for detection of less than one HIV-1 virion,*" J. Virol. Methods 157:122-32; Burbulis I et al. (2005) "*Using protein-DNA chimeras to detect and count small numbers of molecules,*" Nat. Methods 2:31-7; Burbulis I et al. (2007) "*Quantifying small numbers of antibodies with a near-universal protein-DNA chimera,*" Nat. Methods 4:1011-3; Adler M et al. (2003) "*A real-time immuno-PCR assay for routine ultrasensitive quantification of proteins,*" Biochem. Biophys. Res. Commun. 308:240-50).

In addition, the IqPCR technique is well suited for the disclosed microfluidic devices. Such devices may provide for microfluidic droplet Immuno-qPCR for multiplexed detection of trace biomarkers, and the standardization by volume of exhaled droplets. The microfluidic droplet IqPCR of the present invention provides for multiplexed detection of trace biomarkers and quantities of proteins (<1000 total proteins). By comparison, current methodologies (e.g., ELISA) require millions of proteins for detection. As such, the systems and methods of the present invention utilizing IqPCR provide an exponential amplification within an immunoassay, and thus extreme detection sensitivity. Single protein detection is therefore possible using the disclosed IqPCR methodologies.

Figure 3:
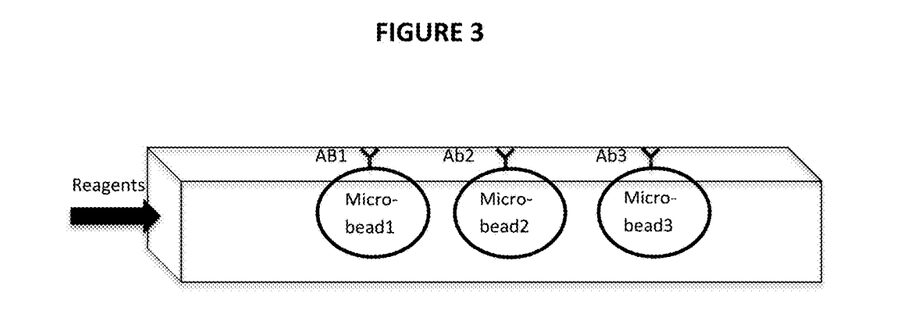
FIG. 3 is a schematic of a multiplexed immunoassay within a microfluidic channel of a microfluidic device according to the present invention.
Figure 4:
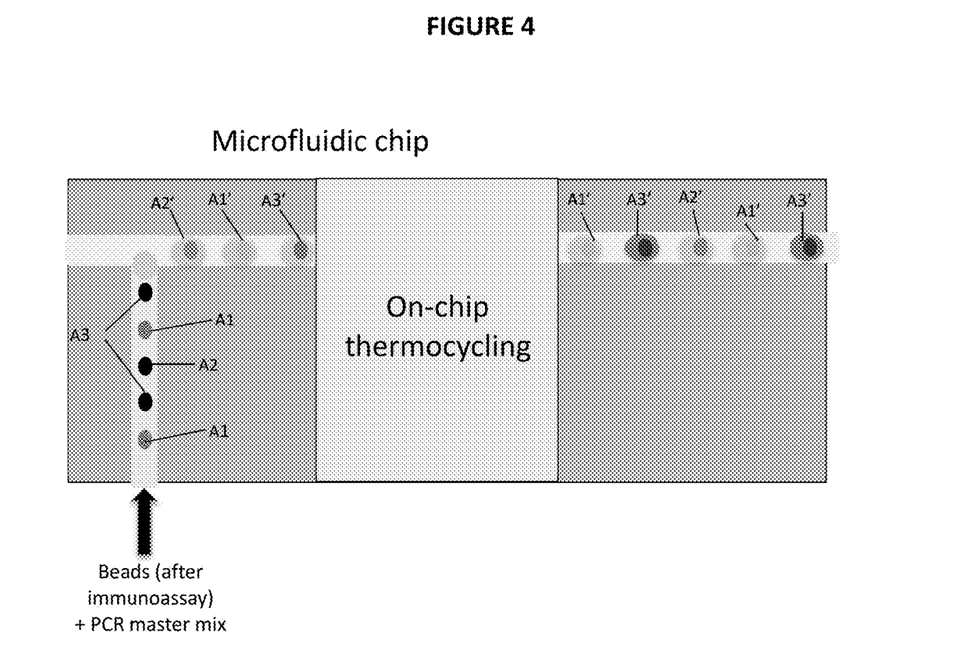
FIG. 4 is a schematic of a microfluidic droplet IqPCR for multiplexed detection of trace biomarkers.

Conventional IqPCR assays are typically done in plates, and thus require a tremendous amount of tedious manual effort. According to aspects of the present invention, chemical immobilization of antibodies into a microfluidic chip is provided (FIGS. 3 and 4). In particular, a novel, multiplexed IqPCR assay in a microfluidic chip is provided, which simultaneously measures multiple targets in each sample. A multiplexed immunoassay is provided within a microfluidic channel of the microfluidic chip. Magnetic microbeads are utilized, which may be held in place during reagent loading and rinses. A relatively high surface area is provided for antibody-antigen reaction as compared to well plates or microfluidic channel walls. Thus, there is no need to immobilize and pattern antibodies within the chip. Conventional multiplex assay systems (e.g., Luminex system) are not compatible with multiplexed IqPCR-PCR product from each bead type must be kept separate.

With reference to FIG. 4, a microfluidic droplet IqPCR assay in a microfluidic chip is provided via an on-chip thereto cycler. The droplet IqPCR provides for the multiplexed detection of various trace biomarkers. Droplet PCR enables isolation of each bead during PCR reaction. Fluorescent droplets after thermal cycling indicates PCR amplification of immuno-label, wherein the particular antigen detected by the microbead is indicated as A1, A2 and A3, and the microbeads impacted in liquid medium are shown as A1', A2' and A3'.

Having generally described the invention, the same will be further understood through reference to the following additional examples, which are provided by way of illustration and are not intended to be limiting of the present invention unless specified.

Cytokine Aerosol Sampling and Recovery from Filters

Various collection methods were tested using generated aerosols of a mixture of six human cytokines including: IFN-gamma, IL-1 beta, IL-7, IL-8, IL-13, and TNF-alpha. (see McKenzie J H et al. (2009) "Use of Teflon filters improves collection efficiency of aerosolized cytokines," Am. J. Respir. Crit. Care Med. 179:A1365; McKenzie J H (2010) "*Methods for environmental endotoxin assay and respiratory biomarker measurement*," Lowell, Mass.: University of Massachusetts Lowell, School of Health & Environment). Cytokines in nebulizer solutions and aerosol samples were assayed using analyte detection LINCOPLEX™ kits (Millipore, Billerica, Mass.) using a Luminex 200 IS system (Luminex Corp. Austin, Tex.). Based on measurements of nebulizer contents before and after experiments, all cytokine aerosols were in the rage of 20-40 pg/$m^3$.

Collection efficiency of two air-to-liquid samplers, the SKC BIOSAMPLER® (SKC Inc, Eighty Four, Pa.) and the OMNI-3000™ wet wall cyclone (Sceptor Industries, Kansas City, Mo.), was compared with that of Teflo 2.0 micron TEFLON® filters (Pall Corp., East Hills, N.Y.). Cytokines were recovered from filters by extraction in 1 mL of 1×PBS, 1% BSA with 0.01% Tween-20. Filter extracts were concentrated before immunoassay using Amicon Ultra-4 3000 MWCO (Millipore, Billerica, Mass.) centrifugal ultra-filtration membranes.

Overall yield from filter collection, extraction, and centrifugal filter concentration was, on average for six cytokines, 26%. TEFLON® filters produced significantly higher yields ($p<0.05$) than did either of the air to liquid samplers (SKC BIOSAMPLER® 4.8%; OMNI-3000™, 5.6%). It is believed that the higher yields from filter extracts reflect that the conventional air-to-liquid samplers did not efficiently collect the small droplets generated by the nebulizer.

Exhaled Breath Respiratory Droplet Sampling and Analysis

In a study of influenza patients, an Exhalair system (Pulmatrix Inc, Lexington, Mass.), which measured particles using an optical particle counter and determined particle concentrations, was utilized to collect particle data on and filter samples of exhaled breath. The vast majority of exhaled particles were found to be in the submicron range, with large inter-individual variation in production rates. Influenza virus RNA, collected on TEFLON® filters, was associated with fine particles (see Fabian P et al. (2008), supra., Plos One 3). Particle generation was subsequently studied from both healthy subjects and subjects infected with human rhinovirus. It was found that respiratory droplets appear to be formed during inhalation, that rate of inhalation and exhalation have little impact, and that production is consistent within a person over time but highly variable between individuals. Therefore, controlling for exhaled particle volume is an important mechanism for standardizing cytokines measured in exhaled breath samples.

By increasing particle output with deep exhalation, combined with the collection of exhaled droplets on TEFLON® filters, the reliable detection of exhaled cytokines was displayed (McKenzie J H (2010), supra., Lowell, Mass.: University of Massachusetts Lowell, School of Health & Environment). Exhaled breath of ten healthy volunteers was collected three times for 20 minutes each. Filters were extracted and assayed using a 12-plex LINCOPLEX™ kit (Millipore, Billerica, Mass.), as described above for the experimental cytokine aerosols. Exhaled particle volume was estimated from optical particle counts (CI-550, Climet Instruments, Redlands, Calif.) made before and after the filter collection while subjects used the same breathing pattern as during the filter collection.

Total estimated particle volume of exhaled particles/20 min ranged from 0.87 to 178 picoliters, with a median of 48 pL. Amounts of IFN-γ, IL-1β, IL-7, and IL-8 were above the limit of detection in ≥50% of samples. Intra-class correlations (ICCs) for these four cytokines were 0.02 (IFN-γ) to 0.34 (IL-1β), using femtogram (fg) of cytokine measured per sample without standardization by respiratory fluid volume. After normalization for particle volume, the ICCs increased and ranged from 0.42 (IL-8) to 0.92 (IL-7), indicating that adjustment for respiratory fluid volume allowed more reliable discrimination between subjects. The results indicate that exhaled droplet volume be used to standardize exhaled biomarker measurements.

Immuno-qPCR Method

IqPCR was implemented for biomarkers including IL-8. Exhaled breath is collected, and IL-8 concentration in exhaled breath with that assayed via IqPCR in the bronchoalveolar lavage fluid (BAL) is compared in 10 subjects with cancer, 10 subjects with COPD, and 10 healthy controls. BAL fluid is thought to be representative of the respiratory tract lining fluid from terminal bronchioles. A concordance of cytokine concentrations from exhaled breath particles and BAL is sought. Physiological maneuvers shown to enhance production of respiratory droplets are utilized.

Filter samples acquired from the Exhalair are utilized. Samples are extraction in 1 mL of 1×PBS, 1% BSA with 0.01% Tween-20. Extracts and breath condensates are concentrated to 100 µl using Amicon Ultra-4 3000 MWCO. To conduct the immunoassay, immuno-detection kits with immuno-magnetic beads are utilized (i.e., magnetic microbeads with antibodies immobilized to the surface). The sample is combined with the immuno-labeled beads (e.g., per manufacturer recommendations). The use of magnetic beads enables simple rinses, which are conducted after each step.

After incubating the sample with the beads and rinsing, biotin-labeled detection antibodies are added, followed by the addition of streptavidin, which binds strongly with all biotin-antibodies immobilized on the beads. Then, biotin-labeled DNA template is added. Because streptavidin has four biotin binding sites, the DNA template is also captured at beads that have been marked by the immuno-label.

For the DNA template, a 104 base-pair sequence primer from the p29 plasmid is utilized. (See Barletta J M et al. (2005), supra., J. Virol. Methods 127:154-64; Barletta J et al. (2009), supra, J. Virol. Methods 157:122-32). Finally, qPCR master mix is added, and qPCR is then run on the sample. This enables an approximate quantification of the number of biomarker molecules that were in the exhaled breath samples.

Study Population

Subjects undergoing bronchoscopy as a part of diagnostic workup for their condition are recruited, as well as normal/healthy controls and COPD/Asthma volunteers. All subjects are age 18 or older. All subjects recruited were able to perform the exhaled breath collection maneuver satisfactorily. Initial studies of lung volumes and exhaled breath particle number were conducted on a convenience sample of persons undergoing routine lung function testing.

Pulmonary Physiologic Measurements and Exhaled Breath Collection

Spirometric measurement of forced expiratory volume at 1 second interval ($FEV_1$), forced vital capacity (FVC), and plethysmographic measurements of total lung capacity (TLC), FRC and RV are performed (University of Maryland Hospital, pulmonary function laboratory). Closing volume is measured by standard inert gas bolus methods in both sitting and supine positions.

In initial experiments, three replicate measurements of exhaled particle numbers were made in the sitting and supine positions, alternating randomly between positions on 20 subjects. For each particle count measurement, the subject was provided a 3-minute exhaled breath sample using the Exhalair. Each subject was instructed to wear a nose clip to prevent nasal and environmental contamination of samples, and instructed to breathe into a mouthpiece according to a specific pattern.

After an initial washout period, software prompts displayed on Exhalair screen instructed each subject to breathe a repeating pattern of tidal breathing at normal lung volumes for 60 seconds followed by an airway closure maneuver requiring repeated exhalation to residual volume for 30 seconds.

In the primary study, each participant provided a particle count measurement with the Exhalair before and after providing three consecutive 20-minute breath samples collected on filters. Three EBC samples were collected using the standard protocol specified for the R-Tube. A nose clip was worn for all count, filter, and EBC collections. Filters and condensate were stored at −80° C. until assayed.

BAL Collection and Analysis

Patients undergoing bronchoscopy and BAL as a part of their diagnostic workup were recruited. In these patients, a small part of the diagnostic SAL sample was obtained. In healthy volunteers and COPD volunteers, the volunteers underwent fiber-optic bronchoscopy with sedation with midazolam and fentanyl and topical anesthetization of the nasopharynx and oropharynx with 2% lidocaine nebulization and jelly. The bronchoscopy and bronchoalveolar lavage was performed and the samples given a code.

The samples were then immediately taken to the lab, where the BAL was first poured through sterile gauze. The cells were then spun down by centrifugation at 1000 g for 10 minutes. The sample was frozen immediately for further analysis. The supernatant and lysed cell pellets were analyzed for cytokine protein level by Luminex assay, and results standardized to the total protein in the supernatant and cell lysate, respectively.

Statistical Data Analysis

Data consist of the following elements: (a) duplicate particle counts in four size ranges and total particle volume measured in sitting and supine positions for each participant in the initial experiments and in one posture for the main experiment; (b) triplicate filter sample cytokine quantification (total mass by immunoassay and concentration normalized as mass divided by total particle volume); (c) triplicate EBC cytokine mass, cytokine concentration in ESC fluid, and estimated normalized by respiratory droplet volume; (d) a single quantification of SAL cytokine concentration; and (e) a measurement of lung volumes.

ANOVA is utilized to analyze the relationship between particle counts in the four size ranges and posture, controlling for lung volumes and age. The relationship of particle volume output to posture, age, and lung volumes is analyzed using linear models, supplemented by generalized additive models as needed to account for non-linear relationships. Intra-class correlation coefficients are computed for both total cytokine mass collected and cytokine concentration adjusted for volume of expired droplets. Correlations between cytokine measurements from in filter samples, EBC samples and BAL samples are examined using both total cytokine mass detected and cytokine concentration in EBC and in respiratory droplets. All statistical computations are performed using SAS (Carey, N.C.) and R (Vienna, Austria).

Discussion

The utilization of IqPCR with immunomagnetic beads may be utilized for the detection of rare biomarker proteins in exhaled breath samples. The measurements have external validity by comparison with BAL.

Further, a highly innovative system for the multiplexed detection of biomarkers in exhaled breath is provided by utilizing a microdroplet qPCR in a microfluidic chip. For the immunoassay, Luminex multi-analyte bead kits are suitable. In these kits, magnetic beads are doped with two different fluorophores, and the relative concentration of each fluorophore is uniquely assigned to the antibody attached to that bead. After performing the DNA-labeled immunoassay, the sample is loaded onto a microfluidic chip that performs microdroplet qPCR. In this technique, the microfluidic chip forms picoliter droplet emulsions from the sample (following the addition of master mix). qPCR is then performed while the droplets are on the chip (see Markey A L et al. (2006) "High-throughput droplet PCR," Methods 50:277-81; Ottesen E A et al. (2006) "*Microfluidic digital PCR enables multigene analysis of individual environmental bacteria*," Science 314:1464-7; Schaerli Y et al. (2009) "Con-*tinuous-flow polymerase chain reaction of single-copy DNA in microfluidic microdroplets*," Anal. Chem. 81:302-6; Srisa-Art M et al. (2009) "High-throughput confinement and detection of single DNA molecules in aqueous microdroplets," Chem. Commun. (Cam b) 6548-50; Wang F and Burns M A (2009) "Performance of nanoliter-sized droplet-based microfluidic PCR," Biomed. Microdevices).

SYSR-green fluorescent images of the droplet indicate whether qPCR occurred within each droplet (a SYBR-green droplet indicates PCR amplification, and thus the presence of the biomarker). Because of the small volume of each droplet, statistically there will be fewer than one bead per droplet, and thus qPCR is performed on individual beads. Therefore, after SYBR-green fluorescent droplets are identified, the bead fluorescence within these drops may be determined. Because of the design of the Luminex beads, the analyte that was detected by IqPCR within that droplet can be identified.

The disclosed methodology may be utilized in the identification of other biomarkers for diagnosis and management of COPD, asthma, lung cancer, tuberculosis (including multi-drug-resistance tuberculosis), and other diseases and disorders.

All publications and patents mentioned in this specification are herein incorporated by reference to the same extent as if each individual publication or patent application was specifically and individually indicated to be incorporated by reference in its entirety. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A method for detecting a biomarker in exhaled breath condensate nanodroplets, comprising the steps of:
   noninvasively collecting exhaled breath condensate (EBC) nanodroplets from a subject by impacting said nanodroplets into a liquid medium; and
   analyzing said nanodroplets utilizing immuno-quantitative polymerase chain reaction (IqPCR) to detect one or more target biomarkers in said nanodroplets.

2. The method of claim 1, wherein at least one of said target biomarkers is associated with a respiratory disease, disorder or infection.

3. The method of claim 2, wherein said respiratory disease, disorder or infection is selected from the group consisting of lung cancer, asthma, chronic obstructive pulmonary disease, tuberculosis, influenza, a human immunodeficiency virus (HIV) related infection, and an acquired immune deficiency syndrome (AIDS) related infection.

4. The method of claim 1, wherein said biomarkers comprise cytokines.

5. The method of claim 4, wherein said cytokines are selected from the group consisting of IFN-gamma, IL-1 beta, IL-7, IL-8, IL-13, and TNF-alpha.

6. The method of claim 1, comprising the further step of determining a volume of said nanodroplets generated by the subject, and standardizing a concentration of said detected biomarkers within said collected nanodroplets.

7. The method of claim 1, wherein the subject is disposed in a supine position during said collecting step.

8. The method of claim 1, comprising the further step of providing a collection device configured for collecting said nanodroplets, said collection device configured to determine the number and size distribution of said nanodroplets.

9. The method of claim 8, wherein said collection device comprises an optical particle counter.

10. The method of claim 1, wherein said IqPCR assay comprises a microbead having an antibody immobilized thereon, wherein said antibody binds to a particular one of said target biomarkers.

11. The method of claim 10, wherein said IqPCR exhibits at least a 10-fold increase in sensitivity in detection of said target biomarkers as compared to enzyme-linked immunosorbent assay (ELISA).

12. The method of claim 11, wherein said IqPCR exhibits at least a 1000-fold increase in sensitivity in detection of said target biomarkers as compared to enzyme-linked immunosorbent assay (ELISA).

\* \* \* \* \*